US005792126A

United States Patent [19]
Tribastone et al.

[11] Patent Number: 5,792,126
[45] Date of Patent: Aug. 11, 1998

[54] FLUID COLLECTION CANISTER FOR USE IN MEDICAL PROCEDURES

[75] Inventors: Daniel N. Tribastone, Charlottesville, Va.; Richard D. Kaufmann, Washington, D.C.; Mark T. Maclean-Blevins, Westminster, Md.; William M. Teringo, Leesburg, Va.

[73] Assignee: Waterstone Medical, Inc., Falls Church, Va.

[21] Appl. No.: 735,697

[22] Filed: Oct. 23, 1996

Related U.S. Application Data

[63] Continuation of Ser. No. 434,704, May 4, 1995, abandoned.

[51] Int. Cl.⁶ .................................................. A61M 1/00
[52] U.S. Cl. .................................................. 604/319; 604/320
[58] Field of Search .......................... 604/118–121, 317, 604/319–323; 600/562, 573; 220/604, 608, 675, 771, 908; 206/519, 520

[56] References Cited

U.S. PATENT DOCUMENTS

| | | |
|---|---|---|
| Re. 33,250 | 7/1990 | Cook. |
| 1,962,192 | 6/1934 | Hapgood. |
| 3,526,316 | 9/1970 | Kalogris ................................ 206/520 |
| 3,680,735 | 8/1972 | Lucas ................................... 220/675 |
| 3,719,197 | 3/1973 | Pannier, Jr. et al.. |
| 3,768,478 | 10/1973 | Fertik et al.. |
| 3,843,016 | 10/1974 | Bornhorst et al.. |
| 3,863,664 | 2/1975 | Holbrook et al.. |
| 4,105,031 | 8/1978 | Kurtz et al.. |
| 4,111,204 | 9/1978 | Hessel. |
| 4,228,798 | 10/1980 | Deaton. |
| 4,275,732 | 6/1981 | Gereg. |
| 4,321,922 | 3/1982 | Deaton. |
| 4,384,580 | 5/1983 | Leviton ................................ 604/319 |
| 4,430,084 | 2/1984 | Deaton. |
| 4,455,140 | 6/1984 | Joslin. |
| 4,487,606 | 12/1984 | Leviton et al. ...................... 604/319 |
| 4,643,107 | 2/1987 | Greene et al.. |
| 4,681,571 | 7/1987 | Nehring. |
| 4,820,284 | 4/1989 | Hauri. |

(List continued on next page.)

FOREIGN PATENT DOCUMENTS

| | | |
|---|---|---|
| 512631 | 5/1955 | Canada. |
| 672582 | 10/1963 | Canada. |

OTHER PUBLICATIONS

Brochure, Bemis Suction Canister Systems, Canisters & Accessories, Feb. 1994.
Brochure, Bemis 800 cc System III, Suction Canister, Feb. 1994.
Brochure, Bemis System III, Suction Canister, Feb. 1994.
Catalog Cut "CRD System", Medi–Vac Corp., 1980.
Photographs of Medi–Vac Guardian System 2000 cc Canister by Baxter Healthcare Corporation (6 photos).

*Primary Examiner*—John G. Weiss
*Assistant Examiner*—David J. Cho
*Attorney, Agent, or Firm*—Banner & Witcoff, Ltd.

[57] ABSTRACT

A medical fluid collection canister for collecting fluids from fluid collection devices in surgical procedures. The medical fluid collection canister includes a receptacle, a lid, and an adapter cap. The receptacle includes a generally a floor portion, and a vertical annular wall portion with a top and a bottom. The lid includes a spout and venting hole, and is attached the top of the annular wall portion for maintaining a vacuum-tight connection therebetween. The annular wall portion, the floor portion, and the lid define a canister interior therebetween. The adapter cap is removably coupled to the spout for maintaining a vacuum-tight connection therebetween. The adapter cap includes a fluid collection device portal fluidly coupled to a fluid collection device, and a vacuum attachment portal fluidly coupled to a vacuum generating device. The canister interior preferably has a volume of 15,000 cubic centimeters, and is sized and arranged to be effective for all medical procedures. Additionally, the canister is adaptable to function as a suction and specimen canister, a suction canister, and a drain canister.

24 Claims, 5 Drawing Sheets

U.S. PATENT DOCUMENTS

| | | |
|---|---|---|
| 4,823,833 | 4/1989 | Hogan et al. . |
| 4,857,042 | 8/1989 | Schneider . |
| 4,857,063 | 8/1989 | Glenn . |
| 4,870,975 | 10/1989 | Cronk et al. ............................ 128/749 |
| 4,925,447 | 5/1990 | Rosenblatt . |
| 4,978,015 | 12/1990 | Walker ...................................... 220/608 |
| 5,185,007 | 2/1993 | Middaugh et al. . |
| 5,254,080 | 10/1993 | Lindsay ...................................... 604/319 |
| 5,307,819 | 5/1994 | Trautmann et al. . |
| 5,382,244 | 1/1995 | Telang . |
| 5,397,299 | 3/1995 | Karwoski et al. . | ions
FLUID COLLECTION CANISTER FOR USE IN MEDICAL PROCEDURES

This application is a continuation of application Ser. No. 08/434,704, filed May 4, 1995 now abandoned.

FIELD OF THE INVENTION

The present invention relates to a collection canister designed for collecting, retaining and transporting fluids. More specifically, the present invention relates to a fluid collection canister for collecting contaminated fluids, which are produced in medical procedures, from floor puddle aspirators, arthroscopic shavers, fluid collecting drapes and other fluid collection devices.

BACKGROUND OF THE INVENTION

Medical collection containers have been used to collect and transport contaminated fluids generated in arthroscopic surgeries and other medical procedures. These prior art containers include open-top buckets which collect fluids from gravity flow, and vacuum canisters with portals which collect fluids from collection devices by applying a vacuum to one of the portals. However, none of these prior art containers has been satisfactory for all surgical procedures.

Open-top buckets have been used to collect contaminated fluids from fluid collection devices in which the fluid flows from the collection devices to the bucket primarily due to the force of gravity. However, open-top buckets pose serious health hazards as objects can possibly fall into the bucket, and contaminated fluids can splash on health care personnel. Further, open-top buckets are difficult to transport, and are susceptible to spilling. Additionally, as open-top buckets are not sealed, they are unable to collect fluids by vacuum.

Prior art vacuum canisters have been unsatisfactory because they are too small for use in all medical procedures. These prior art vacuum canisters typically contain between 800 and 3,000 cc. (cubic centimeters) of fluid. Many surgical procedures which use large quantities of irrigation fluids, e.g., arthroscopic and cystoscopic surgery, have been known to utilize an amount of irrigation fluid significantly in excess of 3,000 cc. In fact, some procedures can generate in excess of 50,000 cc. of fluid. Further, many extended surgical procedures, such as organ harvesting, organ transplants, and open heart surgery, produce significantly more than 3,000 cc. of contaminated bodily fluid. Accordingly, numerous prior art vacuum canisters are required in many surgical procedures. These canisters are painstakingly connected in series and/or demand an extensive amount of attention by health care personnel. This creates the need for an additional health care person, or divides the attention of an existing health care person. Consequently, the patient pays a higher hospital bill and/or potentially receives a lower quality of health care. Further, surgical procedures are frequently interrupted to change the vacuum canisters. These interruptions extend the length of the procedure. As the patient is charged for the use of the operating room on a per minute basis, this increases the amount of the patient's bill. Further, these interruptions could also require the administration of additional anesthesia, possibly placing the patient at an increased health risk.

In addition, small vacuum canisters have been known to come equipped with up to four integrally fixed attachment portals and a permanent float valve positioned in the interior thereof. This creates an additional expensive on a per unit basis, as some applications do not require canisters that include four portals and/or a float valve. Accordingly, the lack of adaptability of the prior art vacuum canisters can result in an increased cost for the patient as he absorbs the cost of paying for features which may not be required.

Further, the prior art vacuum canisters are primarily made of a clear plastic. The clear plastic is formed by polishing the mold for the canister receptacle. However, the clear plastic shows any and all of the scratches and blemishes in the canister receptacle, and some canisters may be rejected at the factory or may be discarded for aesthetic purposes only. This raises the overall costs incurred by the hospital, which are typically passed onto future patients.

SUMMARY OF THE INVENTION

In view of the foregoing, it is a principal object of the present invention to provide an improved multi-functional fluid collection canister which overcomes the problems associated with prior art medical fluid collection canisters.

More specifically, it is an object of the invention to provide a safe and cost-effective fluid canister for all medical procedures.

Another object is to provide an adaptable fluid collection canister which is adaptable for use as a suction and specimen canister, a suction canister, and a drain canister, in which the patient does not have to pay for unnecessary features.

It is yet another object of the invention to provide a fluid canister which is sized to be effective for all medical procedures.

These and other objects are achieved by the present invention which, according to one aspect, provides a medical fluid collection canister for collecting fluids from fluid collection devices used in surgical procedures. The medical fluid collection canister includes a receptacle having a generally vertical annular wall portion and a floor portion, a lid attached to the top of the annular wall portion, and first and second attachment portals. The connection between the lid and the receptacle is vacuum-tight. The wall portion, the floor portion, and the lid define a canister interior therebetween, and a canister exterior. The canister interior has a volume of at least 5,000 cubic centimeters. The first attachment portal connects the canister interior with the canister exterior through the lid, and permits coupling to a fluid collection device. The second attachment portal connects the canister interior with the canister exterior through the lid, and permits coupling to a vacuum generating device.

In another aspect, the invention provides a medical fluid collection vacuum canister for use with a vacuum generating device and a fluid collection device fluidly coupled thereto, for collecting fluids from the fluid collection device by vacuum in surgical procedures. The medical fluid collection vacuum canister includes a receptacle, a lid, and an adapter cap. The receptacle includes a generally vertical annular wall portion with a top and a bottom, and a floor portion. The lid includes a spout and venting hole, and is attached the top of the annular wall portion for maintaining a vacuum-tight connection therebetween. The annular wall portion, the floor portion, and the lid define a canister interior therebetween, and a canister exterior. The canister interior has a volume of at least 5,000 cubic centimeters. The adapter cap is removably coupled to the spout for maintaining a vacuum-tight connection therebetween. The adapter cap includes a fluid collection device portal fluidly coupled to the fluid collection device fluidly connecting the fluid collection device and the canister interior through the lid, and a vacuum attachment portal fluidly coupled to the vacuum generating device fluidly connecting the vacuum generating device and the canister interior through the lid. This arrangement permits the fluid collection device to collect fluid aided by a vacuum generated by the vacuum generating device.

These and other objects and features of the invention will be apparent upon consideration of the following detailed description of preferred embodiments thereof, presented in connection with the following drawings in which like reference numerals identify like elements throughout.

DETAILED DESCRIPTION OF THE PREFERRED EMBODIMENT

Figure 1:
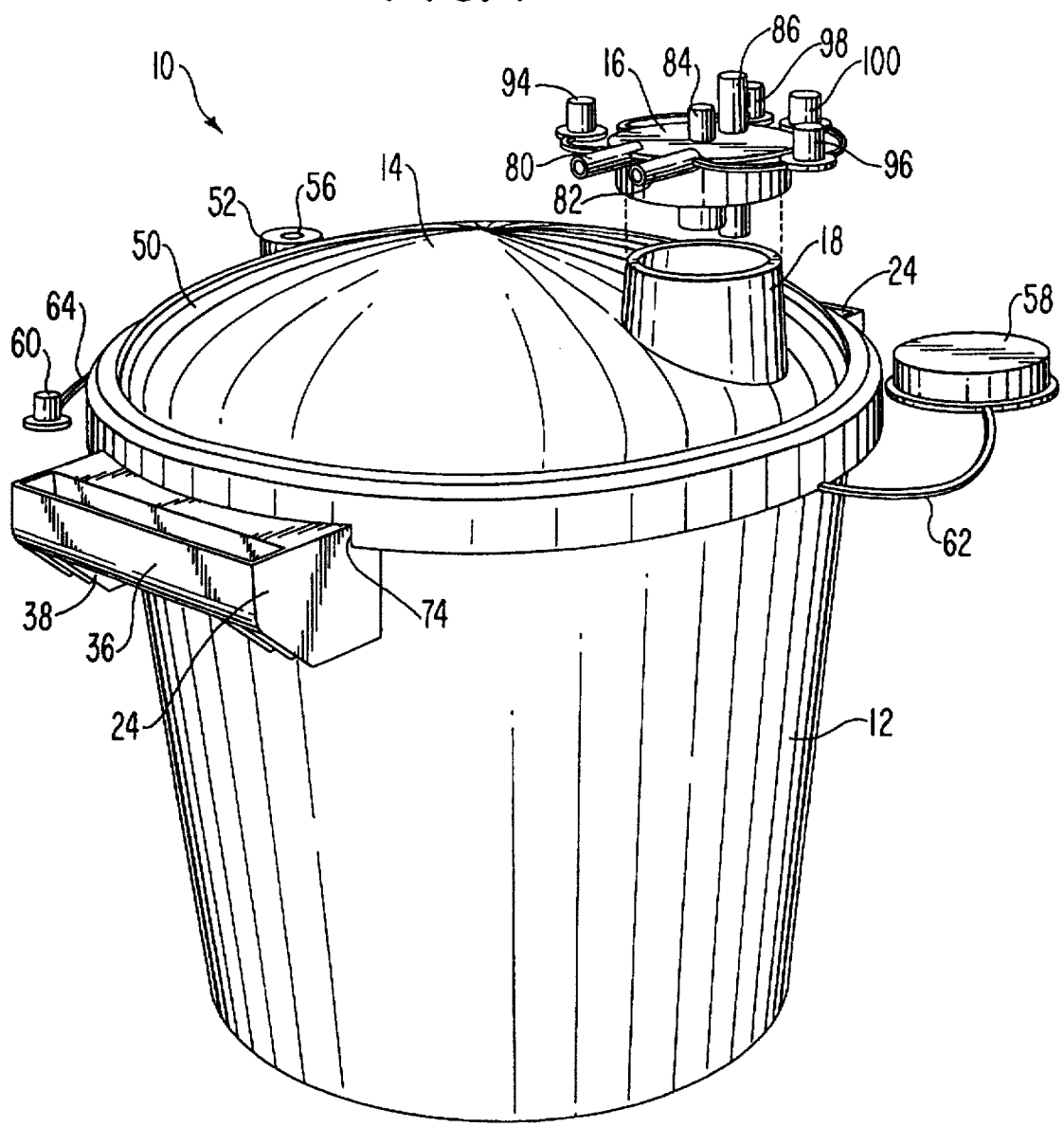
FIG. 1 is a perspective view of the fluid collection canister of the present invention.

In the present invention, as pictured in FIGS. 1–8, a medical fluid collection canister is designated generally by reference numeral 10. Generally, fluid collection canister 10 is a waste collection container designed for use in any surgical procedure which produces large amounts of contaminated fluid. Canister is used to collect fluid from floor puddle aspirators, arthroscopic shavers, fluid collecting drapes, and other fluid collecting devices which can be used for cystoscopic surgery, arthoscopic surgery, or any surgical procedure which uses a large quantity of irrigation fluid. Further, canister 10 can also be very beneficial for use in extended surgical procedures which result in large amounts of contaminated bodily fluid, such as organ harvesting, organ transplants, and open heart surgery. Canister 10 is adaptable to function as (i) a vacuum and specimen canister, in which fluids are collected via an applied vacuum, and shaver specimens are collected in a specimen trap, (ii) a vacuum canister without a specimen trap, and (iii) a drain canister wherein fluids are collected by gravity induced flow.

As shown in FIG. 1, fluid collection canister 10 includes a receptacle 12, a lid 14 and an adapter cap 16 which is used to convert fluid collection canister 10 into a vacuum canister. As described in detail hereinafter, lid 14 is attached to the top of receptacle 12, and adapter cap 16 is removably attached to the top of a spout 18 on lid 14, to form an assembled vacuum canister 10.

Figure 2:
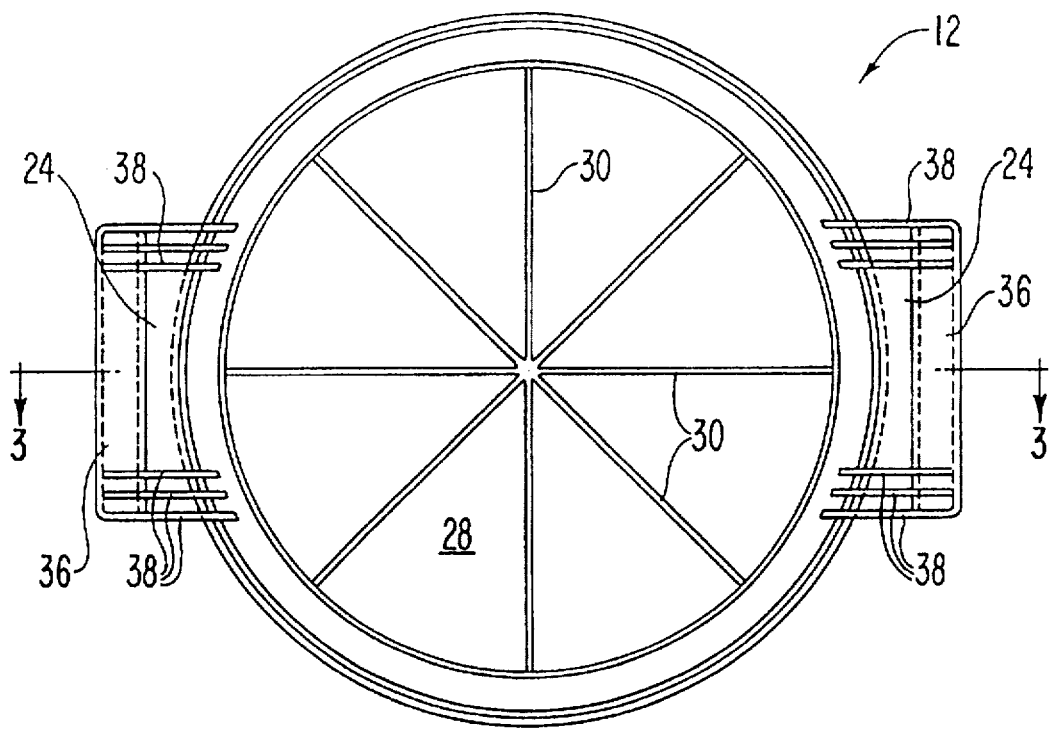
FIG. 2 is a bottom plan view of the receptacle of the fluid collection canister of FIG. 1.
Figure 3:
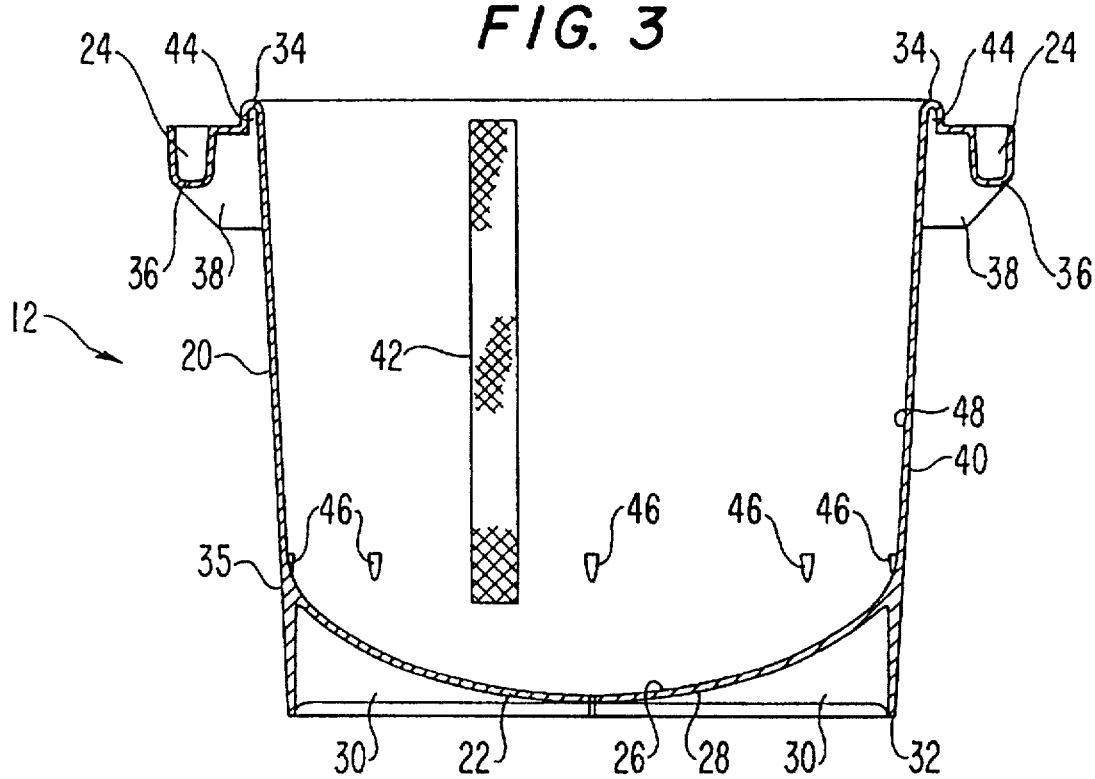
FIG. 3 is a cross-sectional view taken through Line 3—3 of FIG. 2.

As depicted in FIGS. 2 and 3, receptacle 12 includes a generally vertical annular wall portion 20, a floor portion 22, and a pair of opposed gripping handles 24. Annular wall portion 20 and floor portion 22 define a receptacle interior which has a volume slightly larger than 15,000 cc, which is at least 5,000 cc and at least 10,000 cc.

To withstand the forces when receptacle 12 is filled with fluid and a vacuum is applied, floor portion 22 is elliptical, and includes a concave inner surface 26 and a convex outer surface 28. It is recognized that floor portion 22 may be hemispherical or another arcuate shape and still obtain many strength benefits. Additionally, a plurality of radial strengthening ribs 30 extend from convex outer surface 28 to annular wall portion 20. This arrangement of a curved floor 22 and radial strengthening ribs 30 provides enhanced strength permitting canister to contain up to 15,000 cc. of fluid with an applied vacuum attached thereto.

Annular wall portion 20 is tapered slightly outwardly as it extends from its bottom edge 32 to its top edge 34. This tapered design helps provide additional strength, facilitates manufacturing receptacle 12 by injection molding, and permits nesting or stacking as described hereinafter. Floor portion 22 intersects annular wall portion 20 at a point 35 vertically spaced above bottom edge 32 of annular wall portion 20. Thus, bottom edge 32 is a downwardly extending ring which can interface with a circular slot in a dolly, not shown, to facilitate the transport of canister 10. Top edge 34 forms a sealing rim for interfacing with lid 14, as described hereinafter.

Handles 24 are located adjacent to top edge 34 and further facilitates transport. Each handle 24 includes a linear gripping portion 36 and a plurality of connecting plates 38 which are perpendicular to gripping portion 36 and extend between gripping portion 36 and the exterior surface 40 of annular wall portion 20. Connecting plates 38 and gripping portion 36 provide handles 24 with exceptional strength, and permit the safe transportation of a filled canister 10 by its handles 24.

Receptacle 12 is preferably made by injection molding high-impact polystyrene into a mold, where the entire receptacle 12 is formed in a single operation. However, it is recognized that other plastics, and/or manufacturing techniques could be used. In the preferred design, the entire receptacle 12 would have an opaque/frosted appearance except for a crystal clear translucent vertical stripe 42 in annular wall 20. Translucent stripe 42 is sufficient for assessing the fluid level inside canister 10 by health care personnel. The frosted appearance of the remainder of receptacle 12 will: (i) tend to hide many minor scratches and surface blemishes potentially extending to useful life of canister 10, (ii) likely yield a higher percentage of acceptable manufactured units as many small blemishes will be obscured, and (iii) save money over totally clear receptacles, as only a small portion of the mold needs to be polished to obtain a transparent stripe 42, whereas a totally clear receptacle requires a totally polished mold. A label which includes volume delineations and a bio-hazard logo, may be affixed to exterior surface 40.

Receptacle 12 further includes an annular ring support slot 44, and a plurality of internal support projections 46. Ring support slot 44 is formed on the underside of sealing rim 34 and permits canister 10 to be supported solely by a ring support stand, not shown. Internal support projections 46 project from the internal surface 48 of annular wall portion 20 toward the center of receptacle 12, and facilitate the vertical stacking of receptacles 12. To stack receptacles 12, one receptacle 12 is placed inside another receptacle 12, and internal support projections 46 of the lower receptacle support bottom edge 32 of the upper receptacle. To use a receptacle, the upper receptacle is unstacked and mated with a lid 14 as described hereinafter.

Figure 4:
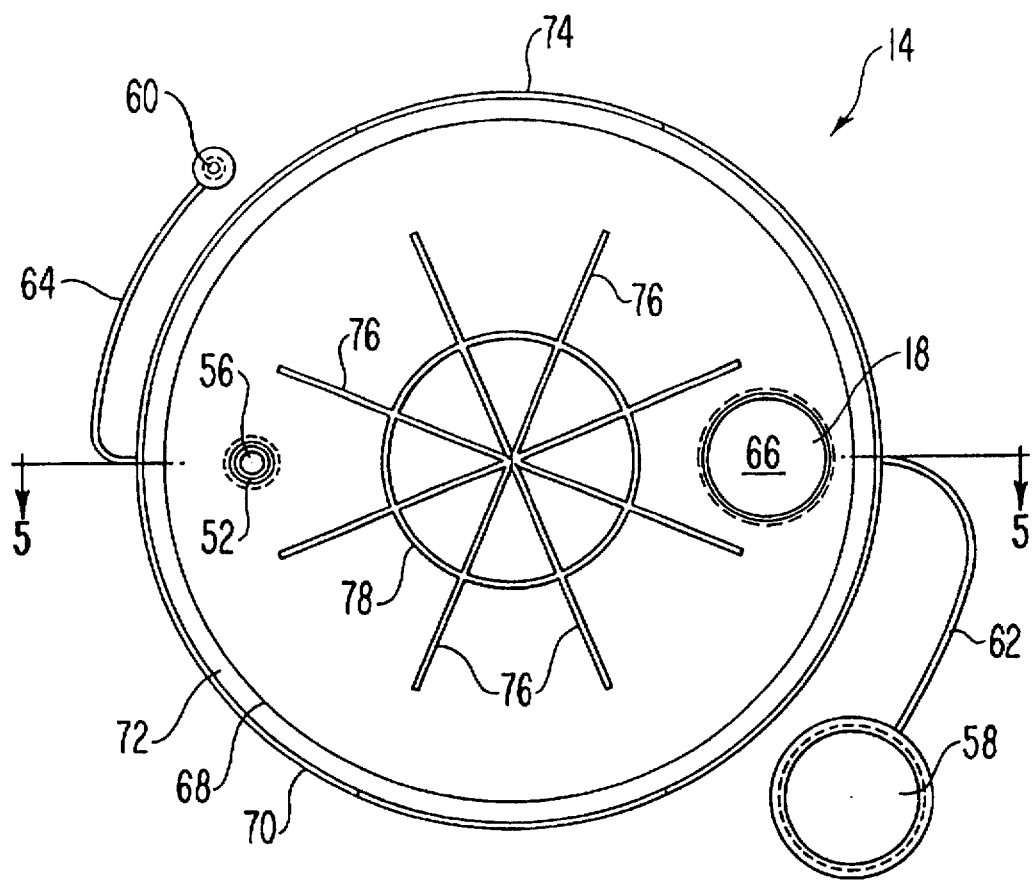
FIG. 4 is a bottom plan view of the lid of the fluid collection canister of FIG. 1.
Figure 5:
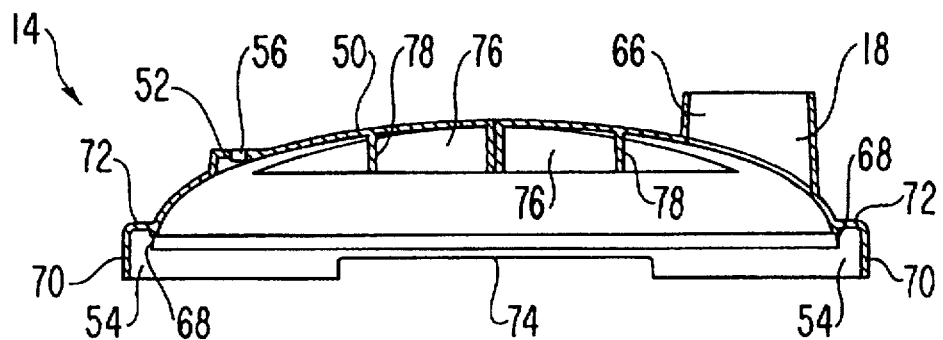
FIG. 5 is a cross-sectional view taken through Line 5—5 of FIG. 4 and shown with the tethered cap for the spout removed.

As shown in FIGS. 4 and 5, lid 14 includes an elliptical top portion 50, a vent 52, a spout 18 and a receptacle interfacing rim 54. The spout or main opening 18 is in the form of a hollow cylinder extending upward from elliptical top portion 50. Spout 18 preferably has a diameter of at least 2 inches to accommodate adapter cap 16 and the features thereon. Vent 52 also has a hole 56 which extends through elliptical top portion 50. However, vent hole 56 is preferably, approximately 0.25 inches in diameter and is used only when pouring out contents to minimize splashing.

Lid 14 further includes tethered sealing caps 58 and 60 attached to an external side portion of interfacing rim 54 by stems 62 and 64, respectively, for sealing spout 18 and vent 52. The caps 58 and 60 are sized to press fit within vent hold 54 and spout 66, respectively. Tethering the sealing caps 58 and 60 prevents the loss or misplacement of the caps, and insures that the caps 58 and 60 are always easily accessible.

Receptacle interfacing rim 54 of lid 14 includes an inner sealing section 68, an outer sealing section 70, and an upper sealing section 72 therebetween. To assemble a lid 14 onto the top of a receptacle 12, lid 14 is snapped, i.e., press-fit, onto sealing rim 34 of receptacle 12, and inner sealing portion 68, outer sealing portion 70, and upper sealing portion 72 seal against the inner, outer, and upper sides, respectively, of sealing rim 34. This seal is fluid and vacuum-tight, and is capable of holding a vacuum and fluids indefinitely. If desired, the sealing surfaces may be toleranced so that once lid 14 is snapped onto receptacle 12, it cannot be removed. Such an arrangement is preferable when users are disposing the canisters after a single use. Additionally, outer sealing portions 70 includes longitudinal cutouts 74 therein to accommodate handles 24.

As previously described, upper portion 50 of lid 14 is preferably domed in an elliptical shape to increase its strength. To further increase its strength, the inside of lid 14 includes radial strengthening ribs 76 and at least one annular strengthening rib 78, as best seen in FIG. 4.

Figure 6:
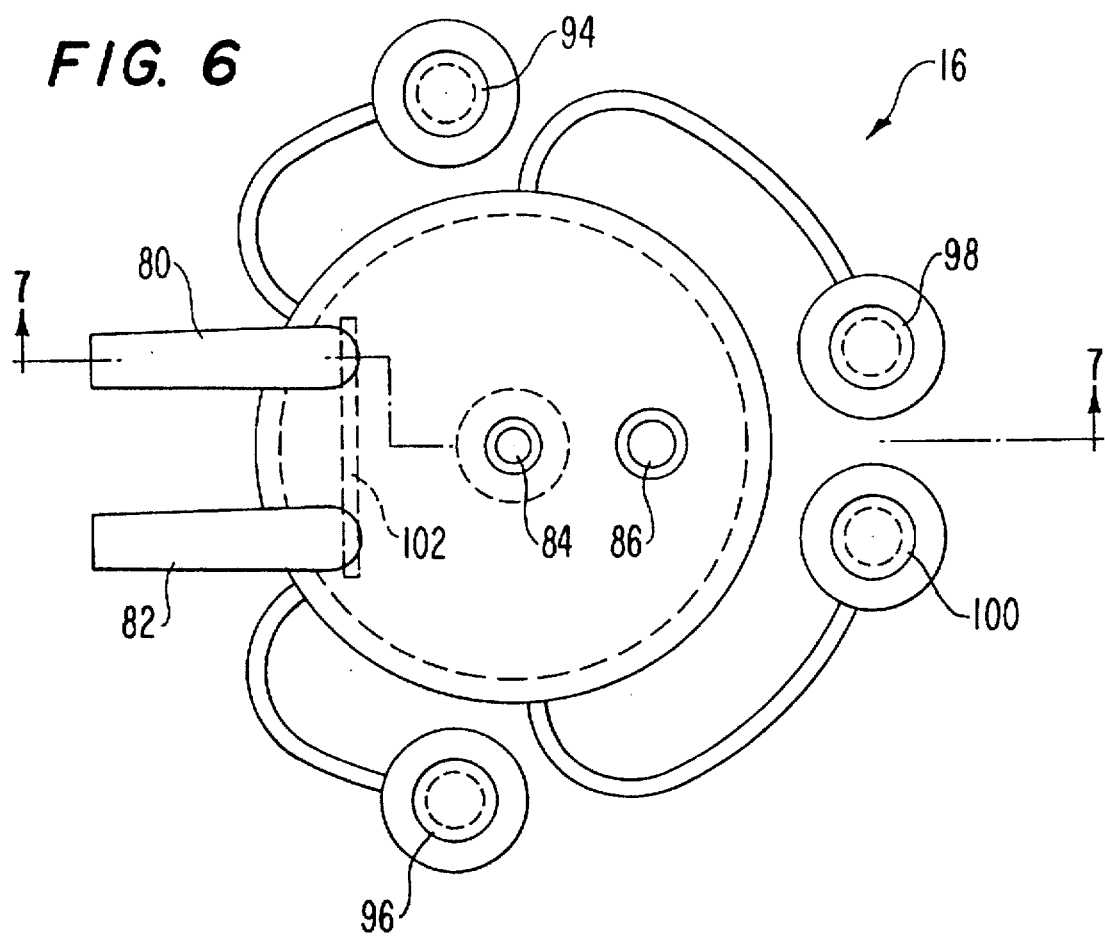
FIG. 6 is a top plan view of the adapter cap of the fluid collection canister of FIG. 1.
Figure 7:
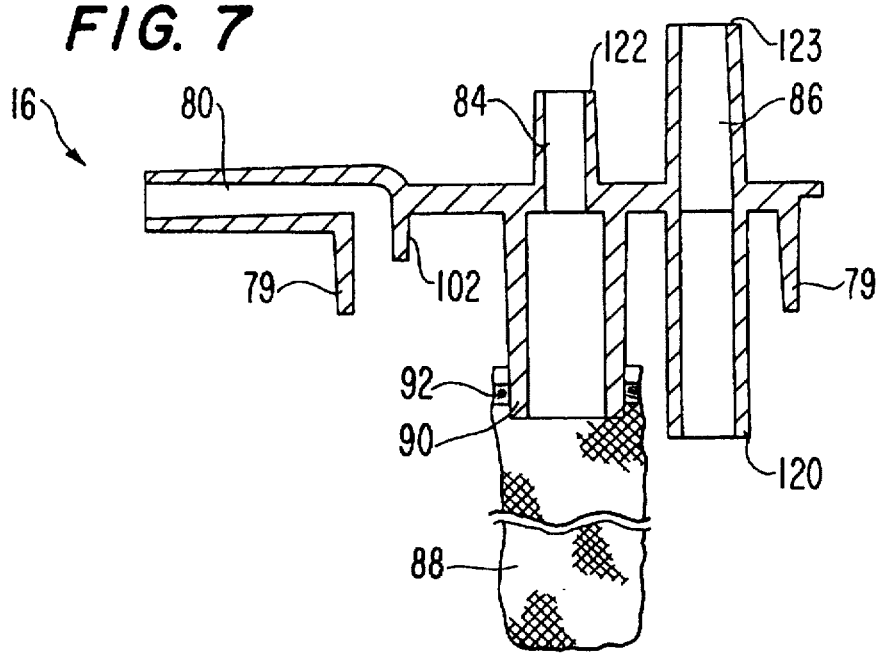
FIG. 7 is a cross-section taken through Line 7—7 of FIG. 6 and shown with the specimen trap attached.

Adapter cap 16 is utilized when canister 10 is implemented to aspirate fluids, i.e., if it is being used as a vacuum canister. Adapter cap 16, attaches to spout 18 in a press-fit arrangement, in which the inside of the side wall 79 of cap 16 fits around the cylindrical rim of spout 18 and creates a liquid and vacuum-tight connection therebetween. As seen in FIGS. 6 and 7, adapter cap 16 includes four portals 80, 82, 84, and 86. Two portals 80 and 82 are for connection to any fluid collection device, and extend from the side of adapter cap 16. Portals 80 and 82 are positioned at 90° to help prevent tube kinking. Another portal 84 extends through the center of cap 16, and may optionally have a specimen trap 88 attached to the lower end 90 thereof, for procedures such as arthroscopic debridements. Specimen traps 88 are sock-like filters and known in the art, and may be connected to lower end 90 by a fastening band 92 or other suitable device. A suction portal 86 also extends through the top of cap 16, and is connected to vacuum tubing coupled to a vacuum generating device, for applying a vacuum to the interior of canister 10. Adapter cap 16 further includes tethered sealing caps 94, 96, 98, and 100 connected to the sides of adapter cap 16, for respectively capping portals 80, 82, 84, and 86 when not in use, or when the procedure has been completed. As with tethered caps 58 and 60, such a tethered arrangement assures easy accessibility of caps 94, 96, 98, and 100, and prevents the loss and misplacement of caps 94, 96, 98, and 100.

Additionally, a fluid blocking wall 102 downwardly deflects fluids entering canister 10 via portals 80 and 82, and prevents the fluids from striking the contents inside specimen trap 88.

Lid 14 and adapter cap 16 are preferably made from injection molded high density polypropylene. However, it is recognized that other plastics and materials which will create a tight seal allowing the canister to hold a vacuum effectively could be used. Additionally, other manufacturing techniques could be used. Further, if desired, adapter cap 16 may also be domed to provide additional strength.

Figure 8:
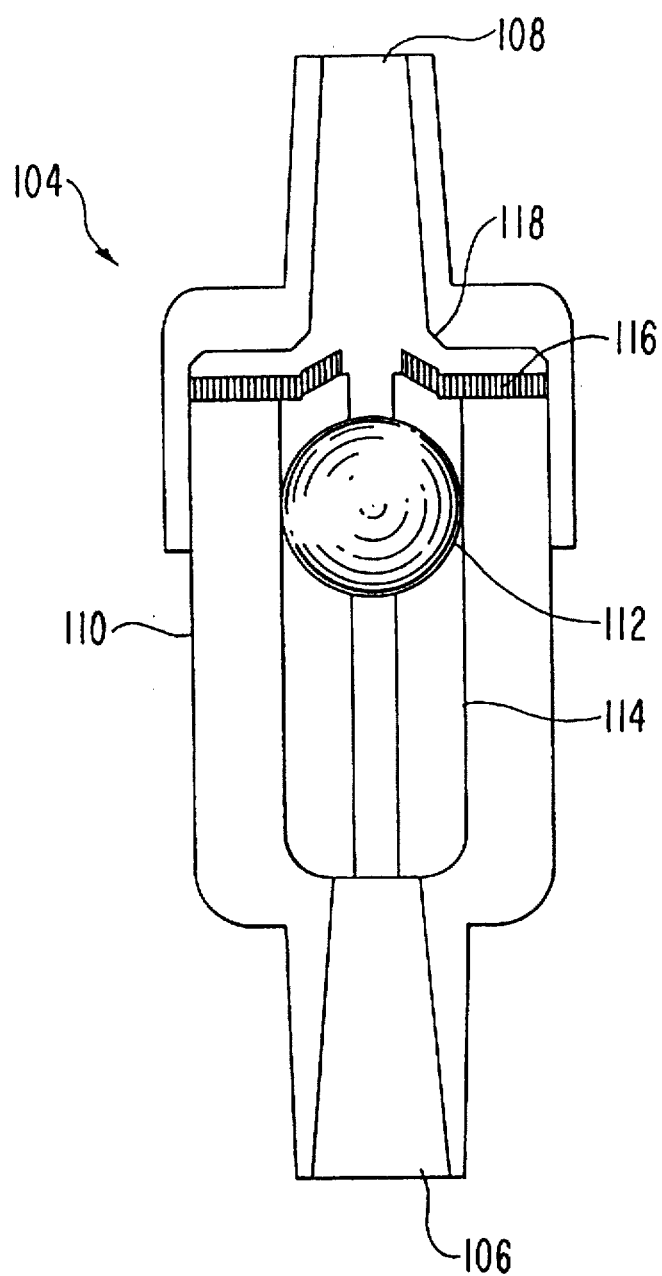
FIG. 8 is a schematic illustration of the removably mountable external float valve.

When canister 10 is used as a vacuum canister, it can be attached to a vacuum generating device without a shut-off valve, or to an existing suction system which includes a shut-off valve. If the former situation exists, a shut-off valve 104, as schematically shown in FIG. 8, is attached to vacuum portal 86 to prevent contaminated fluids from entering the vacuum generating device.

Valve 104 includes valve body 110, a first end 106 for direct removable connection to vacuum portal 86, and a second end 108 for connection to the vacuum generating device via vacuum tubing. Valve body 110 functions in the same manner as a typical float valve. In one arrangement, valve body 110 includes a ball 112, a ball retainer 114, a flexible gasket 116, and an abutment surface 118.

In operation, when the level of fluid inside canister 10 is below the bottom 120 of vacuum portal 86, air is drawn by the vacuum generating device from first end 106 to the second end 108, circumventing ball 112. However, when the level of contaminated fluid reaches the bottom 120 of vacuum portal 86, the fluid is sucked into valve body 110 and ball 112 remains above the fluid as it has a specific density less than the fluid, i.e., it floats. When ball 112 reaches the upper end of ball retainer 114, it deflects elastomer 116 into abutment surface 118, and the ball 112 and elastomer 116 interface creates a seal therebetween. This seal prevents any fluid from being sucked into the vacuum generating device.

It should be recognized that shut-off valve 104 may be designed in numerous different manners as long as it performs the desired functions of permitting the vacuum generating device to apply a vacuum to the canister interior when the level of fluid is below a predetermined level, and preventing the flow of fluid to the vacuum generating device when the level of fluid is above the predetermined level.

In operation, lid 14 is securely press-fitted to receptacle 12 as previously described. If canister 10 is being used as a vacuum and specimen canister, specimen trap 88 is attached to lower end 90 of specimen portal 84. The adapter cap 16 is securely attached to spout 18 with specimen trap 88 extending into the canister. The suction portal 86, is attached, via tubing, to a vacuum generating device for creating a vacuum. The upper end 122 of the specimen portal 84 is coupled to a surgical tool for collecting tissue and bone debris from the patient. None, either, or both of the two remaining portals 80, 82 is coupled to other fluid collecting devices, e.g., floor puddle suckers, fluid collecting floormats, fluid collecting draping, etc. Any unused portal 80, 82 is sealed by a respective cap 94, 96. If canister 10 is coupled to a vacuum system which does not include a valve preventing the flow of fluids into its vacuum generating device, shut-off valve 104 is attached to upper end 123 of the suction portal 86 for accomplishing this objective. However, if the vacuum system includes a shut-off valve between canister 10 and the vacuum generating device, shut-off valve 104 is not necessary. During operation, the vent hole 56 is sealed by cap 60 to maintain the generated vacuum. Fluid is sucked into canister 10 via portals 80, 82, 84, and tissue and bone debris is collected in trap 88. Upon the completion of a surgical procedure, adapter cap 16 with specimen trap 88 is placed inside a sealable container, and sealed and transported to a laboratory for analysis. Spout 18 is then sealed by cap 58, and canister 10 may be safely transported from the operating room. Canister 10 may then be safely emptied via spout 18, or otherwise properly discarded.

If the canister 10 is used as a vacuum canister without the specimen trap, the same arrangement as described above would be used, except that specimen portal 84 would function the same as the two 90° portals 80, 82. Thus, any or all of the three non-suction portals 80, 82, 84 are coupled to fluid collecting devices, and prior to beginning a surgical procedure, the unused portals are sealed by a respective cap 94, 96, 98. Upon the completion of the surgical procedure, all of the portals 80, 82, 84, 86 are capped by their respective sealing cap 94, 96, 98, 100, and canister 10 may be safely transported from the operating room. Canister 10 may then be safely emptied via spout 18, or otherwise properly discarded.

If the canister 10 is used as a drain canister, the adapter cap 16 is not necessary. The spout 18 in lid 14 is open, and tubing one or more fluid collecting devices are extended into the canister interior through spout 18. The fluids flow due to the force of gravity from the fluid collection devices into the canister 10. Upon the completion of a surgical procedure, spout 18 and venting hole 56 are sealed by their respective cap 58, 60, and canister 10 may be safely transported from the operating room. Canister 10 may then be safely emptied via spout 18, or otherwise properly discarded.

Regardless of its intended use, when the surgical procedure has finished, canister 10 is capped and transported out of the operating room, either by manual lifting or pushing it on a dolly. In the event that more than one canister is used, the additional canisters are also transported from the operating room.

This system is therefore advantageous because one canister 10 can potentially replace sixteen prior art vacuum canisters, resulting in a lower cost to the patient and/or better health care services. Further, as canister 10 is adaptable for use as a suction and specimen canister, a suction canister, and a drain canister, the patient does not have to pay for unnecessary features. Additionally, as all of the portals are located on adapter cap 16, canister 10 is easily customizable to interface with machines, tubing and connectors having unique interfaces by merely introducing a differently adapter cap.

While particular embodiments of the invention have been shown and described, it is recognized that various modifications thereof will occur to those skilled in the art. Therefore, the scope of the herein-described invention shall be limited solely by the claims appended hereto.

What is claimed is:

1. A medical fluid collection canister for collecting fluids from fluid collection devices in surgical procedures, said medical fluid collection canister comprising:

a receptacle, said receptacle including a generally vertical annular wall portion and a floor portion, said annular wall portion having a top and a bottom;

a lid attached to said top of said annular wall portion for maintaining a vacuum-tight connection therebetween;

said annular wall portion, said floor portion, and said lid defining a canister interior therebetween, and a canister exterior, said canister interior having a volume of at least 5,000 cubic centimeters;

a first attachment portal connecting said canister interior with said canister exterior through the lid, and permitting a fluid collection device to be fluidly coupled thereto;

a second attachment portal connecting said canister interior with said canister exterior through the lid, and permitting a vacuum generating device to be fluidly coupled thereto; and a plurality of gripping handles integrally molded with said annular wall portion of said canister for manually lifting said canister;

wherein said floor portion of said canister includes an inner concave surface facing the canister interior, and an outer convex surface facing said canister exterior.

2. The medical fluid collection canister of claim 1, wherein said canister interior has a volume of at least 10,000 cubic centimeters.

3. The medical fluid collection canister of claim 2, wherein said canister interior having a volume of at least 15,000 cubic centimeters.

4. The medical fluid collection canister of claim 1, wherein said lid includes a spout, said medical fluid collection canister further comprising an adapter cap removably attached to said spout for maintaining a vacuum-tight connection therebetween, said first and second attachment portals integral with said adapter cap.

5. The medical fluid collection canister of claim 4, further comprising a float valve directly removably coupled to said second attachment portal on the canister exterior.

6. The medical fluid collection canister of claim 4, wherein said integral first attachment portal is 90° displaced from said integral second attachment portal.

7. The medical fluid collection canister of claim 4, further comprising a specimen trap for receiving and containing human tissue and bone shavings, said specimen trap removably coupled to said first attachment portal in the interior of said canister.

8. The medical fluid collection canister of claim 4, further comprising a third attachment portal connecting said canister interior with said canister exterior through the lid, and permitting a fluid collection device to be fluidly coupled thereto, and a fourth attachment portal connecting said canister interior with said canister exterior through the lid, and permitting a fluid collection device to be fluidly coupled thereto, said third and fourth attachment portals integral with said adapter cap.

9. The medical fluid collection canister of claim 1, wherein said lid includes an inner concave surface facing the canister interior, and an outer convex surface facing said canister exterior, and further comprising a plurality of radial strengthening ribs and at least one annular strengthening rib located on said inner concave surface of said lid.

10. The medical fluid collection canister of claim 1, wherein the interior surface of said annular wall portion includes a plurality of protrusions which project into the interior of the canister, wherein a plurality of canisters can be vertically stacked by supporting the bottom of the annular wall portion of an upper canister on the protrusions of a lower canister.

11. The medical fluid collection canister of claim 1, wherein said lid further includes a venting hole to permit use of the canister as a drain canister.

12. The medical fluid collection canister of claim 1, wherein said floor portion is structurally coupled to said annular wall portion above the bottom of the annular wall portion.

13. The medical fluid collection canister of claim 1, wherein said annular wall portion is predominantly opaque and further includes a generally vertical transparent portion.

14. A medical fluid collection canister for collecting fluids from fluid collection devices in surgical procedures, said medical fluid collection canister comprising:

a receptacle, said receptacle including a generally vertical annular wall portion and a floor portion, said annular wall portion having a top and a bottom;

a lid attached to said top of said annular wall portion for maintaining a vacuum-tight connection therebetween;

said annular wall portion, said floor portion, and said lid defining a canister interior therebetween, and a canister exterior, said canister interior having a volume of at least 5,000 cubic centimeters;

a first attachment portal connecting said canister interior with said canister exterior through the lid, and permitting a fluid collection device to be fluidly coupled thereto; and a second attachment portal connecting said canister interior with said canister exterior through the lid, and permitting a vacuum generating device to be fluidly coupled thereto, wherein said floor portion of said canister includes an inner concave surface facing the canister interior, and an outer convex surface facing said canister exteriors;

the canister further including a plurality of radial strengthening ribs extending between the outer convex surface of said floor portion and said annular wall portion.

15. The medical fluid collection canister of claim 14, wherein the floor portion of said canister is substantially elliptical.

16. The medical fluid collection device of claim 14, wherein the annular wall portion extends below the floor portion and forms a downwardly extending ring for supporting the canister.

17. The medical fluid collection canister of claim 14, wherein said canister interior has a volume of at least 10,000 cubic centimeters.

18. A medical fluid collection canister for collecting fluids from fluid collection devices in surgical procedures, said medical fluid collection canister comprising:

a receptacle, said receptacle including a generally vertical annular wall portion and a floor portion, said annular wall portion having a top and a bottom;

a lid attached to said top of said annular wall portion for maintaining a vacuum-tight connection therebetween;

said annular wall portion, said floor portion, and said lid defining a canister interior therebetween, and a canister exterior, said canister interior having a volume of at least 5,000 cubic centimeters;

a first attachment portal connecting said canister interior with said canister exterior through the lid, and permitting a fluid collection device to be fluidly coupled thereto;

a second attachment portal connecting said canister interior with said canister exterior through the lid, and permitting a vacuum generating device to be fluidly coupled thereto; and a plurality of gripping handles integrally molded with said annular wall portion of said canister, for manually lifting said canister.

19. The medical fluid collection canister of claim 18, wherein each said gripping handle includes a gripping member for manual grasping, and a plurality of strengthening ribs extending between each said gripping member and said annular wall portion of said canister.

20. The medical fluid canister of claim 18, wherein said lid includes cutouts therein to receive said gripping handles.

21. The medical fluid collection canister of claim 18, wherein said canister interior has a volume of at least 10,000 cubic centimeters.

22. A medical fluid collection canister for collecting fluids from fluid collection devices in surgical procedures, said medical fluid collection canister comprising:

a receptacle, said receptacle including a generally vertical annular wall portion and a floor portion, said annular wall portion having a top and a bottom;

a lid attached to said top of said annular wall portion for maintaining a vacuum-tight connection therebetween;

said annular wall portion, said floor portion, and said lid defining a canister interior therebetween, and a canister exterior, said canister interior having a volume of at least 5,000 cubic centimeters;

a first attachment portal connecting said canister interior with said canister exterior through the lid, and permitting a fluid collection device to be fluidly coupled thereto; and a second attachment portal connecting said canister interior with said canister exterior through the lid, and permitting a vacuum generating device to be fluidly coupled thereto, wherein said lid is void of integral vacuum portals and fluid collection device portals.

23. The medical fluid collection device of claim 22, wherein said lid is devoid of either integral vacuum portals and fluid collection device portals.

24. A medical fluid collection canister for collecting fluids from fluid collection devices in surgical procedures said medical fluid collection canister comprising:

a receptacle, said receptacle including a generally vertical annular wall portion and a floor portion, said annular wall portion having a top and a bottom;

a lid attached to said top of said annular wall portion for maintaining a vacuum-tight connection therebetween;

said annular wall portion, said floor portion, and said lid defining a canister interior therebetween, and a canister exterior, said canister interior having a volume of at least 5,000 cubic centimeters;

a second attachment portal connecting said canister interior with said canister exterior through the lid, and permitting a vacuum generating device to be fluidly coupled thereto, and a float valve directly removably coupled to said second attachment portal on the exterior of the canister.

* * * * *